United States Patent [19]

Eldridge

[11] 4,409,991

[45] Oct. 18, 1983

[54] FLUID FLOW CONTROL DEVICE FOR USE WITH AN EVACUATED BLOOD COLLECTION CONTAINER

[75] Inventor: William N. Eldridge, Rutherford, N.J.

[73] Assignee: Becton Dickinson and Company, Paramus, N.J.

[21] Appl. No.: 330,342

[22] Filed: Dec. 14, 1981

Related U.S. Application Data

[62] Division of Ser. No. 118,158, Feb. 4, 1980, Pat. No. 4,319,582.

[51] Int. Cl.³ ............................................. A61B 5/14
[52] U.S. Cl. ................................... 128/766; 604/246
[58] Field of Search .................. 128/766, 760, 214 R, 128/274; 251/8; 604/246, 207, 187, 181, 93

[56] References Cited

U.S. PATENT DOCUMENTS

| | | | |
|---|---|---|---|
| 2,309,302 | 1/1943 | Butler et al. | 128/214 R |
| 2,471,623 | 5/1949 | Hubbell | 128/214 R |
| 4,280,509 | 7/1981 | Bethkenhagen et al. | 128/766 |

FOREIGN PATENT DOCUMENTS 1586087  2/1970  France .......................... 128/766

*Primary Examiner*—John D. Yasko

[57] ABSTRACT

A fluid flow control device for use with an evacuated blood collection container comprises a substantially rigid body. Two needle cannulae are connected to the body with a space therebetween. A resilient, collapsible passage member lies in the space and connects the two cannulae in fluid communication with each other. The passage member contacts the body only at its ends with its central portion positioned to remain free of contact with the body during use. This passage member is accessible to finger grip from at least two different directions to allow an operator of the device to apply pressure with the fingers to control fluid flow through the passage member.

Another embodiment of the present invention substantially as described above includes an operable collapsing element connected to the body for collapsing the passage member during use to control fluid flow therethrough.

1 Claim, 6 Drawing Figures

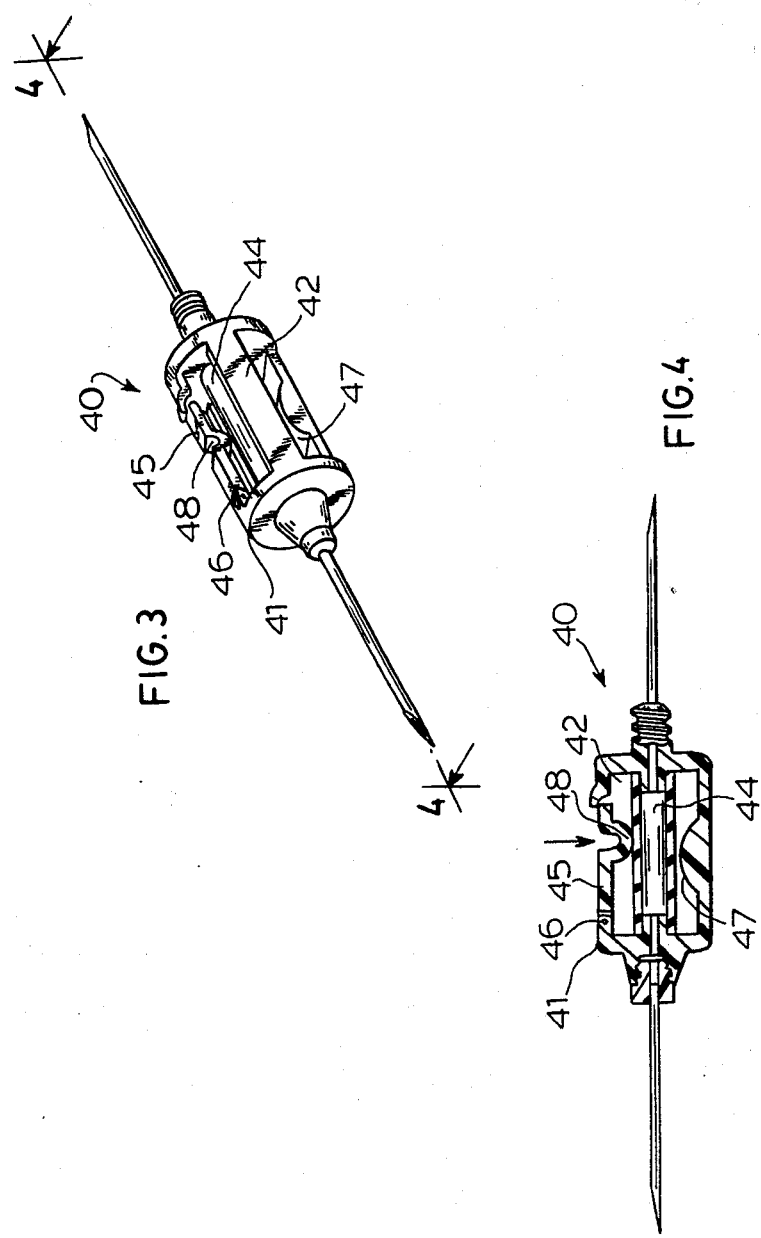

FLUID FLOW CONTROL DEVICE FOR USE WITH AN EVACUATED BLOOD COLLECTION CONTAINER

This is a division of application Ser. No. 118,158, filed Feb. 4, 1980, now U.S. Pat. No. 4,319,582.

BACKGROUND OF THE INVENTION

The present invention relates generally to a fluid flow control device for use with an evacuated blood collection container in the collection of blood from a patient, and more particularly, concerns a fluid flow control device for such use which is operable to control the vacuum pressure applied through a blood collecting needle cannula.

In the procedure of collecting blood from a patient, the collection operator generally has no effective control over the flow of blood from the patient into the evacuated blood collection container. This is due to the fact that the blood collection devices generally known and used in today's market have no provision to provide such control. Control of blood flow becomes particularly important in those instances when veins collapse or occlude the needle.

These situations arise more frequently nowadays since most blood is collected from a patient with the use of an evacuated blood collection container. If a patient should have a weak vein, the high initial vacuum in the blood collection container is believed to suck the vein wall against the bevel of the needle or collapse the vein itself, whereby blood flow ceases. With no mechanism available to shut off the vacuum, the operator generally resorts to some makeshift means of dealing with the situation, ranging from rotating the needle while in the vein to removing the evacuated blood container altogether. Of course, the needle rotation could be very traumatic to the patient, while removal of the needle altogether will require a second attempt to make the blood collection. Accordingly, there is a need for valving or throttling the evacuated blood collection container so as to have an effective control of the vacuum applied to the patient's vein.

One such vacuum blood drawing device is disclosed in U.S. Pat. No. 3,491,748. In that patent, the device allows the vein to refill by blocking the vacuum from the evacuated blood container by pressing a flexible tube against a control surface, the pressure being applied by the thumb of the operator. The overall construction of this patented device is somewhat complicated and could add expense to its manufacture. In addition, reliance upon the projecting pressure surface in conjunction with the flexible tube for flow control raises the possibilities of misalignment and perhaps unnecessary bulk to this type of device. Therefore, there is still a need for further improvements in this type of device which controls the vacuum pressure from an evacuated blood collection container during the blood collecting procedure.

SUMMARY OF THE INVENTION

A fluid flow control device for use with an evacuated blood collection container in the collection of blood from a patient comprises a substantially rigid body. A first needle cannula is connected to the body and is adapted to penetrate the vein of a patient. A second needle cannula is connected to the body and is adapted to penetrate a stopper in an evacuated blood collection container. The first and second needle cannulae are connected to the body with a space in between. Connecting the first and second cannulae in the intermediate space is a resilient, collapsible passage member which places the first and second cannulae in fluid communication with each other. The passage member contacts the body only at its ends with its central portion positioned in the space to remain free of contact with the body during use. The passage member is accessible to finger grip from at least two different directions to allow an operator of the device to apply pressure with the fingers to control fluid flow through the passage member.

In another general embodiment of the present invention substantially as described above, operable means is connected to the body for collapsing the passage member during use to control fluid flow therethrough. This operable means takes the place of the finger grip control associated with the previously described embodiment. One specific embodiment of this type includes a pivotally attached lever as the operable means, adapted to contact the passage member upon being depressed. Another specific embodiment of this type includes a spring-loaded actuator as the operable means adapted to contact the passage member upon being depressed. And a further specific embodiment of this type includes a wheel device to roll against the passage member for collapsing the same during use. Of course, other operable elements to satisfy this function fall within the purview of this invention.

It can be seen that all embodiments of the present invention are structurally different from any previous devices serving the function described herein, including that device described in U.S. Pat. No. 3,491,748. The present invention is simple and straightforward to use, and can be fabricated inexpensively in line with the disposability requirements of single use needles for blood collecting procedures. Furthermore, the present invention allows its operator to effectively control the vacuum pressure being applied to the vein of the patient from the evacuated blood collection container. In addition to control of the vacuum pressure, the present invention provides the operator with the ability to control the rate of fluid flow by constricting the passage through which the blood flows into the collection container. Other advantages of the present invention are offered as well.

BRIEF DESCRIPTION OF THE DRAWINGS

FIG. 3 is a perspective view illustrating an alternative embodiment of the fluid flow control device of the present invention;

FIG. 4 is a cross-sectional view taken along line 4—4 of FIG. 3;

DETAILED DESCRIPTION

Figure 1:
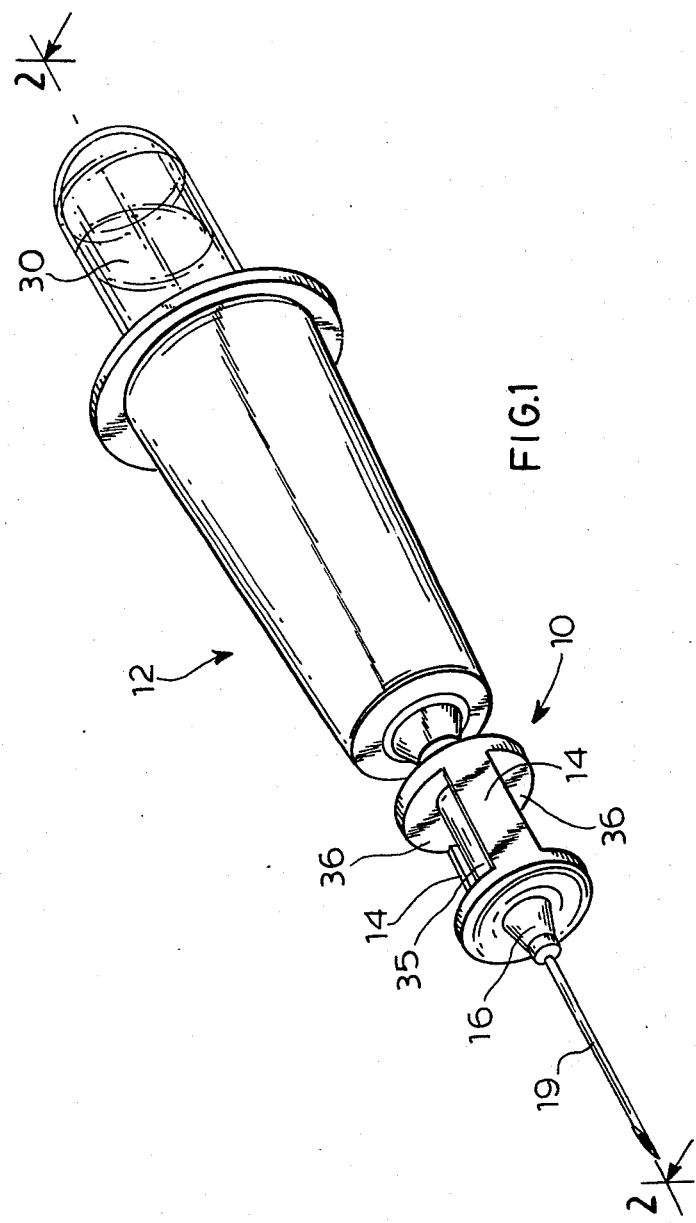
FIG. 1 is a perspective view of the preferred fluid flow control device illustrated assembled into a blood collection assembly.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be pointed out in the appended claims.

Figure 2:
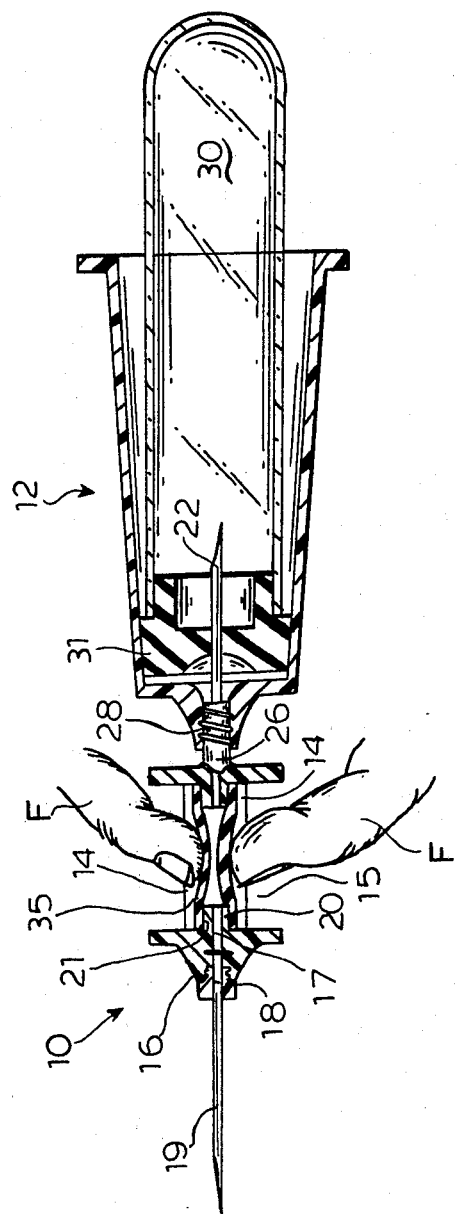
FIG. 2 is a cross-sectional view taken along line 2—2 of FIG. 1.

Referring to the drawings, particularly FIGS. 1 and 2, there is illustrated a fluid flow control device 10 assembled to a blood collection assembly 12. Control device 10 includes a body 14 which in the embodiment being described has a generally cylindrical shape. It is substantially rigid so that sufficient structural integrity is provided during use of this invention. Body 14 is formed with a hollow space 15 inside. Rigid plastic or metal are the preferred materials to be used in fabricating the body of the present device.

At one end of body 14 is a protrusion 16 which includes an internal threaded section 18. A first needle cannula 19 with mating threads is connected to body 14 by being threaded into protrusion 16. This feature allows different size needles to be connected to the fluid flow control device for different applications. It is appreciated that the needle cannula may be connected to body 14 by means other than the threading engagement. Needle cannula 19 is intended to penetrate a vein of a patient and is preferably connected to body 14 substantially along the longitudinal axis of the fluid flow control device. The opposite side of protrusion 16 includes a protruding nipple 20 within space 15 inside the hollow body. A hollow channel 17 extends through the protrusion/nipple portion of body 14 for a fluid path therethrough. At the innermost end of nipple 20 is an opening 21 so that fluid can travel through needle cannula 19 and channel 17 into the fluid flow control device.

At the other end of body 14 and connected thereto is a second needle cannula 22. Needle cannula 22 is also preferably located along the longitudinal axis of control device 10 and is preferably positioned to be in substantial axial alignment with first needle cannula 19. Needle cannula 22 also terminates inside space 15 in the hollow body in a protruding nippe 24. An opening 25 is at the innermost end of nipple 24 to provide for fluid flow through needle cannula 22. A short protrusion 26 with external threads 28 surrounds needle cannula 22 adjacent body 14. These external threads are selected to mate with internal threads on a standard blood collection assembly 12. Included in blood collection assembly 12 is an evacuated blood collection container 30 which includes a penetrable stopper 31. As seen particularly in FIG. 2, second needle cannula 22 penetrates stopper 31 so that blood may flow into the blood collection container.

Connecting both needle cannulae into fluid communication with each other is a resilient, collapsible hollow tube 35 which serves as a passageway for the fluid to flow from needle cannula 19 to needle cannula 22. Tube 35 is connected only at its ends to body 14; specifically, one end of the tube is attached to nipple 20, while the other end of the tube is attached to nipple 24, thereby extending across hollow space 15 inside the body. The central portion of tube 35 is thus spaced sufficiently away from the walls of body 14 so as to remain free of contact with any portion of the body, particularly during use. It is preferred that hollow tube 35 be formed of an elastomeric material in order to impart the desired resilient, collapsible characteristics.

To gain access to tube 35 two windows 36 are provided through the peripheral surface of body 14, the windows being substantially opposed to each other on opposite sides of tube 35 while communicating with space 15 inside the body. These windows are sufficiently large to allow the fingers F of an operator, such as indicated in FIG. 2, to reach inside of body 14 to contact tube 35. In operation, needle cannula 19 penetrates the vein of a patient during the blood collecting procedure. As soon as evacuated blood collection container is inserted into the collection assembly, the vacuum pressure therein causes a drawing action through both needle cannulae and the fluid flow control device. If for some reason the vein of the patient becomes collapsed or needle 19 is otherwise occluded, the present invention allows the operator to terminate the vacuum applied to needle cannula 19. The operator need only squeeze resilient tube 35 with his fingers to effectively serve as a valve to shut off the vacuum pressure from the evacuated collection container. While holding the resilient tube in a collapsed condition, the vein of the patient is allowed to fill up with blood once again so that the blood collecting procedure can continue by the operator merely releasing his hold on tube 35. By use of this fluid flow control device in the blood collecting assembly, effective vacuum control is provided, thereby eliminating the need to perhaps remove the needle from the vein of the patient as has been done previously. It is pointed out that those skilled in the art will recognize that fluid flow control device 10 may take on other configurations than those illustrated in the drawings; particularly, the axial alignment of the needle cannulae may be modified as well as the number and type of openings or windows to provide finger access inside the body of the device. For example, one large window may be provided for finger access instead of a plurality of openings.

Alternative embodiments to the previously described fluid flow control device are illustrated in FIGS. 3 through 6. Turning specifically to FIGS. 3 and 4 in which one of the alternative embodiments is illustrated, fluid flow control device 40 in most respects is the same as the embodiment just described, except that it includes an operable element for collapsing the resilient passage tube during use to control fluid flow therethrough. Particularly, body 41 has at least one window opening 42 for gaining access to resilient, collapsible hollow tube 44 within. A depressible lever 45 is pivotally connected to body 41 by means of a pivot pin 46. Lever 45 has a downwardly extending depression 48 which serves as a contact surface against tube 44. In use, the operator depresses lever 45 downwardly so that depression 48 contacts tube 44 and squeezes the same. In this fashion, tube 44 is collapsed against the body of the device lying underneath the tube. To facilitate this collapsing effect, body 41 includes a protrusion 47 projecting upwardly toward hollow tube 44. Protrusion 47 is located on the body opposite from the depression on the lever so that squeezing contact is maximized. As soon as the operator releases depressible lever 45, the resiliency of hollow tube 44 allows it to spring back to its normal condition. Thus, in this embodiment, the operator needs to use only thumb control for controlling the fluid flow through the control device.

Figure 5:
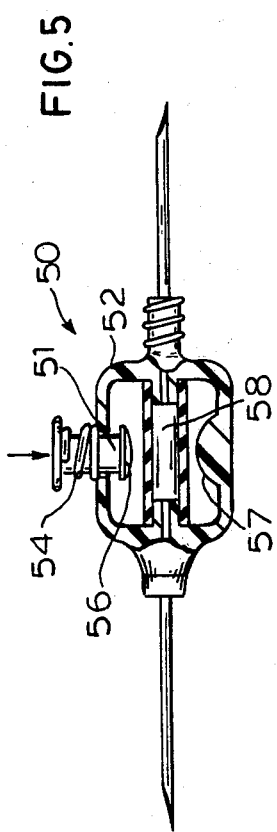
FIG. 5 is a cross-sectional view similar to FIG. 4 but illustrating an alternative mechanism for fluid flow control.

Referring now to FIG. 5, another embodiment is illustrated in which an alternative operable mechanism is provided for collapsing the resilient passage tube. In this embodiment the fluid flow control device 50 includes a button-type actuator 51 mounted through a hole in the wall of body 52. A spring 54 is positioned between the wall of body 52 and a flange 55 on button actuator 51. It can be seen that downward depression of actuator 51 will cause its bottom surface 56 to come in contact with the resilient, collapsible hollow tube 58 inside body 52. This downward depression of the actuator against the hollow tube will cause it to collapse against a protrusion 57 on the wall of the body lying underneath the hollow tube. Once again, effective fluid flow control is provided by this embodiment.

Figure 6:
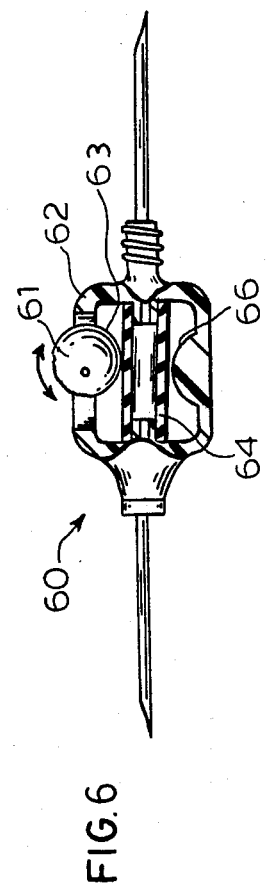
FIG. 6 is a cross-sectional view similar to FIG. 4 but illustrating another alternative mechanism for fluid flow control.

Fluid flow control device 60 illustrated in FIG. 6 represents another embodiment which includes an operable mechanism for collapsing the resilient passage tube within the fluid flow control device. In this embodiment, a thumb wheel 61 is connected to body 62 so that by a rolling motion it will roll against resilient, collapsible passage tube 64 for collapsing same during use. Wheel 61 includes an off-set cam surface 63 so that, by rotation, the wheel can contact collapsible hollow tube 64 inside the body. A protrusion 66 on the inside wall of the bodies lies underneath the hollow tube opposite the wheel to facilitate the collapse of the tube.

Thus, a fluid flow control device is provided for use with an evacuated blood collection container in the collection of blood from a patient in which the operator can control the vacuum drawing force which is applied to the vein of a patient, and diminish or terminate that vacuum force by the control mechanism of this invention.

What is claimed is:

1. Blood sample flow control apparatus for controlling the flow of blood from a vein after an evacuated blood collection container has been connected thereto for collecting said blood sample, characterized by
   (a) an elongated substantially rigid body;
   (b) a first needle cannula connected to said body for penetrating said vein;
   (c) a second needle cannula connected to said body at the end thereof opposite said first cannula for penetrating the stopper of said evacuated blood collection container;
   (d) a resilient collapsible tube in said elongated body interconnecting said first and second cannulae;
   (e) said collapsible tube providing a continuous flow passage from said vein to said blood collection container upon said blood collection container being connected to said second needle cannula;
   (f) a depressible lever pivotally mounted on said body and operable to collapse said tube after said blood collection container has been connected to said second needle cannula to control flow of blood through said tube;
   (g) first abutment means on said lever for engaging said tube; and
   (h) second abutment means on said body on the side thereof opposite said first abutment means for cooperating to collapse said tube.

* * * * *